United States Patent
Li et al.

(10) Patent No.: US 8,957,210 B2
(45) Date of Patent: Feb. 17, 2015

(54) METHOD FOR SYNTHESIZING 1-(2-FLUOROBENZYL)-1H-PYRAZOLO[3,4-B]PYRIDINE-3-FORMAMIDINE HYDROCHLORIDE

(71) Applicant: Pharmablock (Nanjing) R&D Co., Ltd., Jiangsu (CN)

(72) Inventors: Jin Li, Jiangsu (CN); Xiaoyu Yang, Jiangsu (CN); Jingwei Zhu, Jiangsu (CN); Minmin Yang, Jiangsu (CN); Xihan Wu, Jiangsu (CN)

(73) Assignee: Pharmablock (Nanjing) R&D Co., Ltd. (CN)

( * ) Notice: Subject to any disclaimer, the term of this patent is extended or adjusted under 35 U.S.C. 154(b) by 0 days.

(21) Appl. No.: 14/364,040

(22) PCT Filed: Nov. 28, 2012

(86) PCT No.: PCT/CN2012/085451
§ 371 (c)(1),
(2) Date: Jun. 9, 2014

(87) PCT Pub. No.: WO2013/086935
PCT Pub. Date: Jun. 20, 2013

(65) Prior Publication Data
US 2014/0309425 A1 Oct. 16, 2014

(30) Foreign Application Priority Data
Dec. 12, 2011 (CN) .......................... 2011 1 0414004

(51) Int. Cl.
*C07D 471/04* (2006.01)
(52) U.S. Cl.
CPC ................................. *C07D 471/04* (2013.01)
USPC ........................................................ 546/119
(58) Field of Classification Search
USPC ........................................................ 546/119
See application file for complete search history.

(56) References Cited

U.S. PATENT DOCUMENTS

| 2002/0173514 | A1 | 11/2002 | Stasch et al. | 514/256 |
| 2011/0092479 | A1 | 4/2011 | Ahrendt et al. | 514/210.21 |
| 2011/0225969 | A1 | 9/2011 | Larose, Jr. et al. | 60/605.1 |

FOREIGN PATENT DOCUMENTS

| CN | 1555374 | 12/2004 | ............ A61K 31/505 |
| CN | 102149712 | 8/2011 | ............ A61K 31/437 |
| CN | 102191974 | 9/2011 | .............. F01N 3/025 |
| CN | 102491974 | 6/2012 | ............ C07D 471/04 |
| WO | WO 2010/051561 | 5/2010 | ............ A61K 31/497 |
| WO | WO 2011/147810 | 12/2011 | ............ C07D 471/04 |
| WO | WO 2011/149921 | 12/2011 | .............. A01N 43/90 |
| WO | WO 2012/143813 | 10/2012 | ............ C07D 471/10 |
| WO | 2013/030288 | * 3/2013 | |

OTHER PUBLICATIONS

Liang, L. et al. "Synthesis of riocihuat in the treatment of pulmonary hypertension" *Chinese Journal of Medicinal Chemistry*, vol. 21 No. 2, Apr. 2011 p. 120-125, with English abstract (7 pgs).

Mittendorf, Dr. et al. "Discovery of Riociguat (BAY 63/2521): A Potent, Oral Stimulator of Soluble Guanylate Cyclase for the Treatment of Pulmonary Hypertension" *ChemMedChem* vol. 4, Issue 5, pp. 853-865 May 11, 2009, Abstract only (4 pgs).

International Search Report issued in corresponding PCT Patent Appln. Serial No. PCT/CN2012/085451 dated Mar. 7, 2013 with English translation (8 pgs).

* cited by examiner

*Primary Examiner* — Niloofar Rahmani
(74) *Attorney, Agent, or Firm* — Hayes Soloway P.C.

(57) ABSTRACT

The present invention relates to the field of chemical synthesis, and in particular to a method for synthesizing 1-(2-fluorobenzyl)-1H-pyrazolo[3,4-b]pyridin-3-formamidine hydrochloride, which is an important intermediate of Riociguat that is an anti-thromboembolic-disease medicine. The method is characterized in that: 3-iodo-1H-pyrazolo[3,4-b]pyridine is used as a raw material; the raw material is reacted with fluorobenzyl bromide to form a compound (10); the compound (10) is reacted with zinc cyanide to form a compound (6); the compound (6) is reacted with sodium methoxide, ammonium chloride, acetic acid and methanol to form a compound (8); and the compound (8) is reacted with chlorine hydride gas to form 1-(2-fluorobenzyl)-1H-pyrazolo[3,4-b]pyridin-3-formamidine hydrochloride. The method has the characteristics of cheap and readily available raw materials, high yield, mild reaction conditions and the like, and is a synthesis method having a large-scale preparation value.

6 Claims, No Drawings

METHOD FOR SYNTHESIZING 1-(2-FLUOROBENZYL)-1H-PYRAZOLO[3,4-B]PYRIDINE-3-FORMAMIDINE HYDROCHLORIDE

FIELD OF THE INVENTION

The present invention relates to the field of chemical synthesis, and particularly to a method for synthesizing 1-(2-fluorobenzyl)-1H-pyrazolo[3,4-b]pyridine-3-formamidine hydrochloride, which is an important intermediate of antithromboembolic disease medicine Riociguat.

BACKGROUND OF THE INVENTION

Riociguat can be used to treat chronic thromboembolic pulmonary hypertension (CTEPH) or pulmonary hypertension, which has a structural formula as follows:

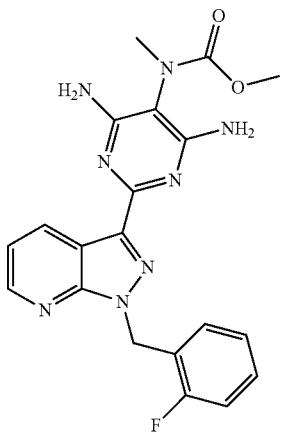 [SMILES: COC(=O)N(C)c1c(N)nc(-c2nn(Cc3ccccc3F)c3ncccc23)nc1N]

Chem. Med. Chem. 2009, 4, 853-865 reports the following method:

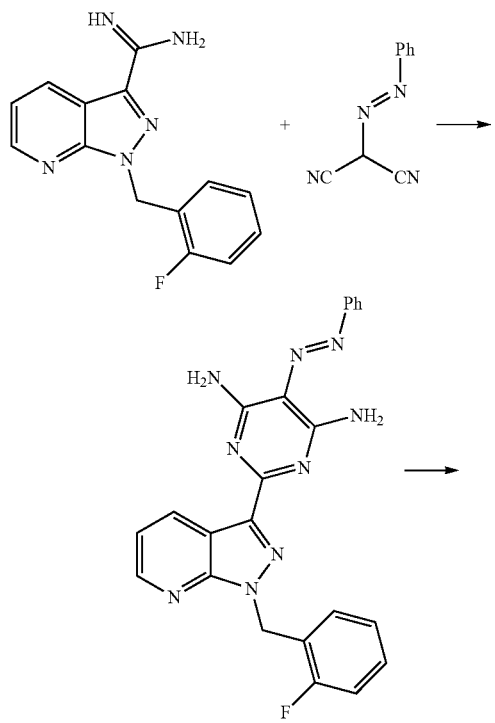

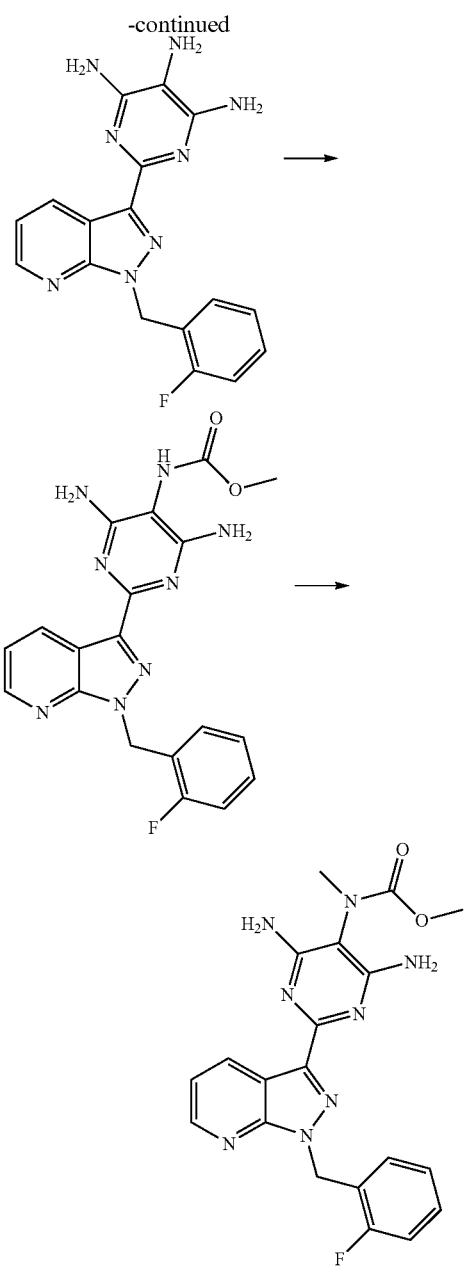

1-(2-fluorobenzyl)-1H-pyrazolo[3,4-b]pyridine-3-formamidine hydrochloride is an important intermediate for synthesis of Riociguat.

In respect to the preparation of 1-(2-fluorobenzyl)-1H-pyrazolo[3,4-b]pyridine-3-formamidine (hereinafter referred to as "compound 8") hydrochloride (hereinafter referred to as "compound 11"), US20020173514 reports the following method:

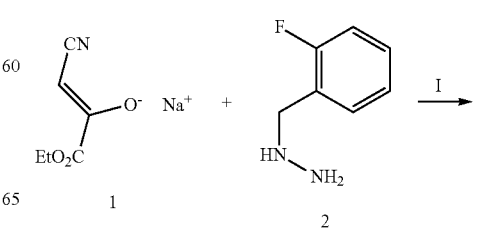

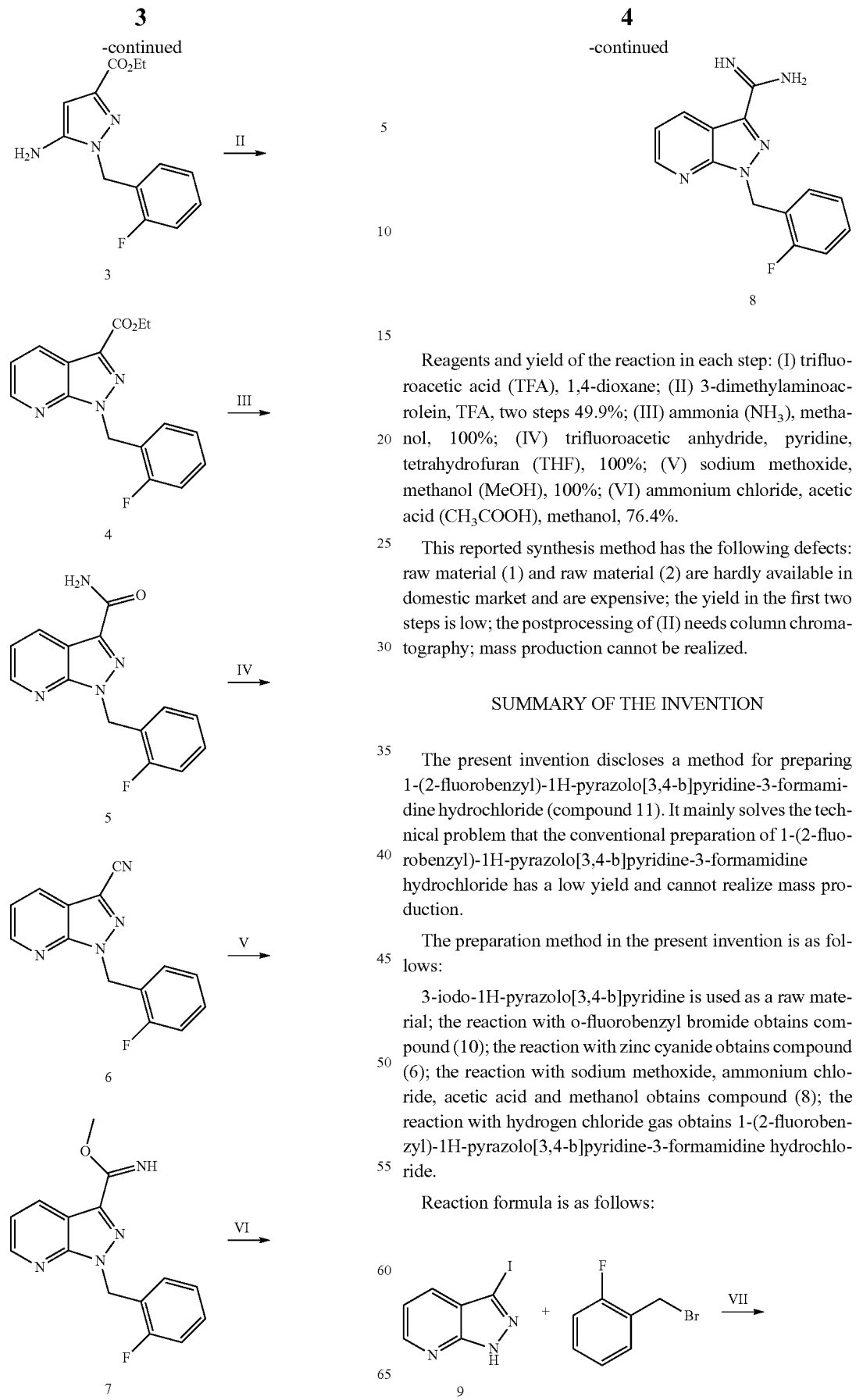

Reagents and yield of the reaction in each step: (I) trifluoroacetic acid (TFA), 1,4-dioxane; (II) 3-dimethylaminoacrolein, TFA, two steps 49.9%; (III) ammonia (NH₃), methanol, 100%; (IV) trifluoroacetic anhydride, pyridine, tetrahydrofuran (THF), 100%; (V) sodium methoxide, methanol (MeOH), 100%; (VI) ammonium chloride, acetic acid (CH₃COOH), methanol, 76.4%.

This reported synthesis method has the following defects: raw material (1) and raw material (2) are hardly available in domestic market and are expensive; the yield in the first two steps is low; the postprocessing of (II) needs column chromatography; mass production cannot be realized.

SUMMARY OF THE INVENTION

The present invention discloses a method for preparing 1-(2-fluorobenzyl)-1H-pyrazolo[3,4-b]pyridine-3-formamidine hydrochloride (compound 11). It mainly solves the technical problem that the conventional preparation of 1-(2-fluorobenzyl)-1H-pyrazolo[3,4-b]pyridine-3-formamidine hydrochloride has a low yield and cannot realize mass production.

The preparation method in the present invention is as follows:

3-iodo-1H-pyrazolo[3,4-b]pyridine is used as a raw material; the reaction with o-fluorobenzyl bromide obtains compound (10); the reaction with zinc cyanide obtains compound (6); the reaction with sodium methoxide, ammonium chloride, acetic acid and methanol obtains compound (8); the reaction with hydrogen chloride gas obtains 1-(2-fluorobenzyl)-1H-pyrazolo[3,4-b]pyridine-3-formamidine hydrochloride.

Reaction formula is as follows:

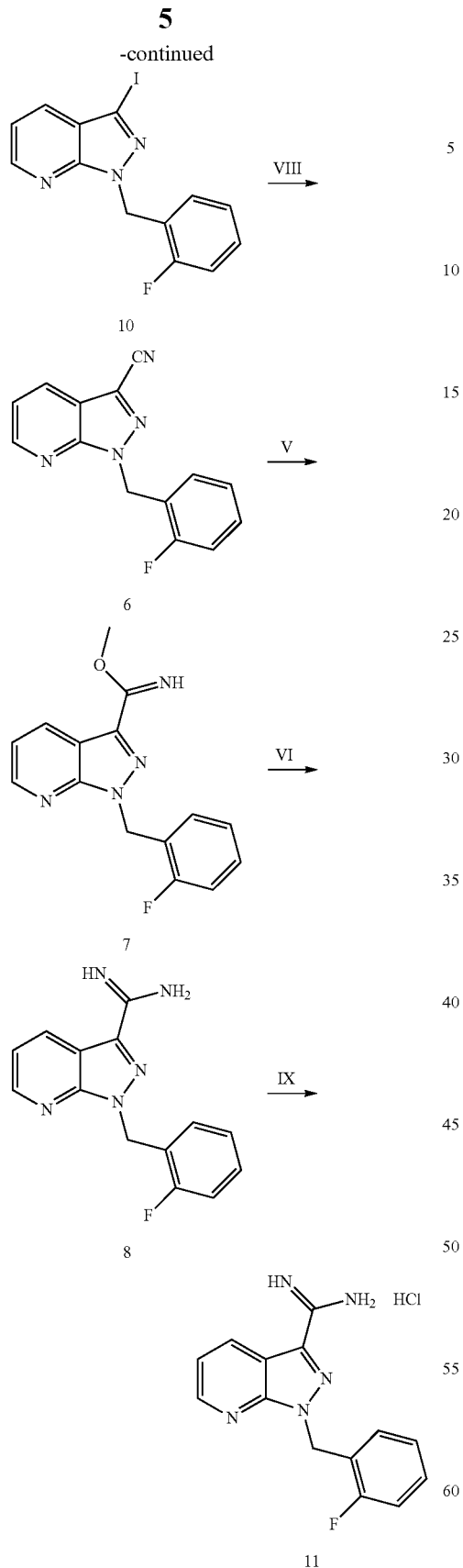

Wherein: The reaction condition in step VII: add potassium carbonate;

The reaction condition in step VIII: add zinc powder, zinc cyanide, 1,1'-bis(diphenylphosphine) ferrocene (dppf) and tetra(triphenylphosphine)palladium(0) (Pd(PPh$_3$)$_4$);

The reaction condition in step V: add methanol and sodium methoxide;

The reaction condition in step VI: add ammonium chloride and acetic acid;

The reaction condition in step IX: add hydrochloric acid or input hydrogen chloride.

The molar ratio of compound (9), o-fluorobenzyl bromide and potassium carbonate is preferably: 1:1.0~1.5:1.5~3.0.

In step VII, the reaction solvent is preferably THF, N,N-dimethylformamide (DMF) or dimethylsulfoxide (DMSO), more preferably DMF.

In step VIII, the reaction temperature is preferably 100~150° C. and the reaction solvent is preferably N,N-dimethylacetamide (DMAC).

In step VIII, the molar ratio of compound (10) and zinc cyanide is preferably 1:0.7~1:1.2.

In step IX, the reaction solvent is preferably methyl tertiary butyl ether (MTBE).

The innovative points of the preparation method provided in the present invention are: 3-iodo-1H-pyrazolo[3,4-b]pyridine is used as a raw material, which is cheap and easily available. In the first step, it may react with o-fluorobenzyl bromide at room temperature in the presence of potassium carbonate (K$_2$CO$_3$) to obtain compound (10), with a yield of 71.16%; in the second step, the reaction with zinc cyanide and others obtains compound (6), with a yield of 63.7%; in the third step, the reaction with sodium methoxide, ammonium chloride, acetic acid and methanol obtains compound (8); in the fourth step, the reaction with hydrogen chloride gas obtains 1-(2-fluorobenzyl)-1H-pyrazolo[3,4-b]pyridine-3-formamidine hydrochloride. The total yield of the last two steps is 99%. This method features cheap and easily available raw materials, high yield and moderate reaction conditions. It is a synthesis method with a value of large-scale preparation.

DETAILED DESCRIPTION OF THE EMBODIMENTS

Example 1

Synthesis of Compound (10)

Add 400 g (1.63 mol, 1.0 eq) of 3-iodo-1H-pyrazolo[3,4-b]pyridine, 369 g (1.96 mol, 1.2 eq) of o-fluorobenzyl bromide and 450 g (3.27 mol, 1.5 eq) of K$_2$CO$_3$ dissolved in 4 L of DMF into a 5 L 4-neck flask and react for 10 h at room temperature. Pour the reaction solution into water after thorough reaction as monitored by TLC, stir it to appear a plenty of grey solid, filter and recrystallize PE: EA=5:1 to obtain 411 g of light yellow solid. The yield is 71.16%.

$^1$H NMR (400 MHz, CDCl3) δ (ppm): 8.62 (d, 1H), 7.85 (d, 1H), 7.27 (dd, 1H), 7.11 (dd, 1H); 6.96-7.08 m, 3H), 5.82 (s, 2H).

Synthesis of Compound (6)

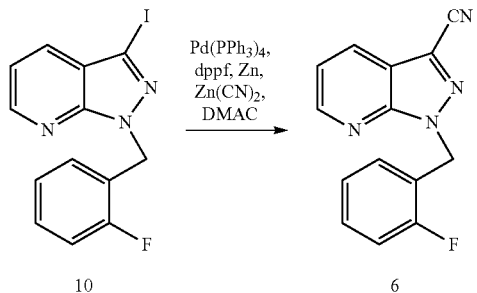 [SMILES: Fc1ccccc1Cn1nc(I)c2cccnc21 ; N#Cc1nn(Cc2ccccc2F)c2ncccc12]

Add 625 g (1.77 mol, 1.0 eq) of compound (10), 11.8 g (0.18 mol, 0.1 eq) of zinc power, 49.1 g (0.0885 mol, 0.05 eq) of dppf, 145.6 g (1.24 mol, 0.7 eq) of Zn(CN)$_2$, 208 g (0.18 mol, 0.1 eq) of Pd(PPh$_3$)$_4$ and 7.5 L of DMAC into a 10 L 4-neck flask in turn, heat them till 120° C. and react for 13 h. Add 12 L of DCM after thorough reaction as monitored by TLC and wash it with a plenty of water. Extract the aqueous layer with DCM, merge the organic phases, dry with anhydrous sodium sulfate, remove a half of solvent through reduced pressure distillation, pass an appropriate amount of silica gel layer, filter, wash with dichloromethane and concentrate to obtain 272 g of light yellow solid. The yield is 63.7%.

$^1$H NMR (400 MHz, CDCl3) δ (ppm): 8.73 (d, 1H); 8.23 (dd, 1H); 7.39 (dd, 1H); 7.26-7.33 (m, 2H); 7.03-7.19 (m, 2H); 5.83 (s, 2H).

Synthesis of Compound (8)

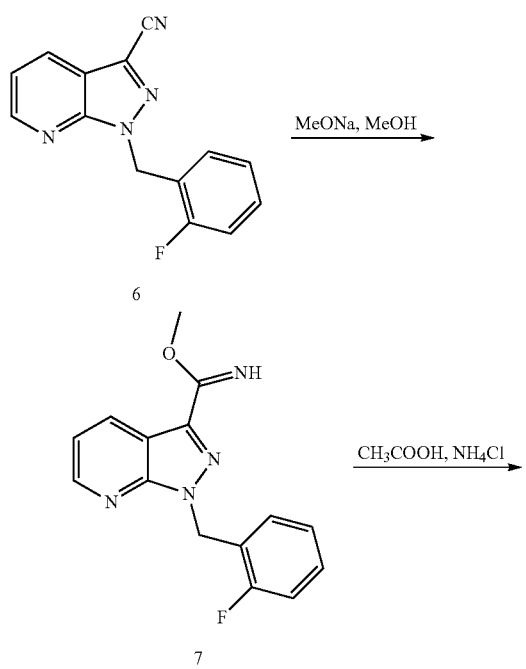

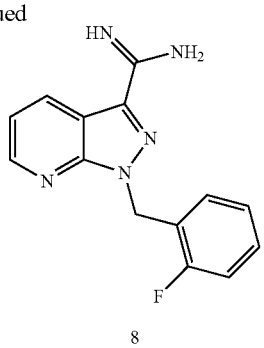

Add 919.7 g (3.646 mol, 1.0 eq) of compound (6) and 7 L of MeOH into a 10 L 4-neck flask, add 295 g (5.469 mol, 1.5 eq) of MeONa under stirring, stir 2 h at room temperature, add 329 g (5.469 mol, 1.5 eq) of CH$_3$CO$_2$H and 293 g (5.469 mol, 1.5 eq) of NH$_4$Cl after that TLC indicates the raw material has disappeared and been completely converted into intermediate (7), adopt heating reflux and take reaction overnight, lower the temperature after thorough reaction as monitored by TLC to appear a plenty of solid, filter and wash with DCM to obtain 981 g of white solid, which is compound (8), and directly used in next step.

Synthesis of Compound (11)

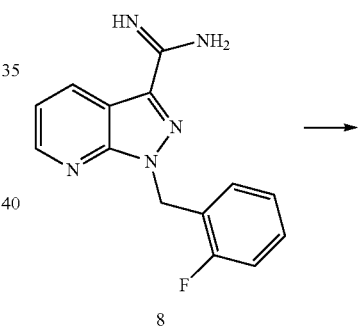

Add 981.0 g (3.646 mol, 1.0 eq) of compound (8) into 5 L of MTBE, stir to form a suspension, input HCl gas for about 2.5 h, filter, wash with DCM and dry to obtain 1103.7 g of white solid. The total yield in the two steps is 99.0%. The purity is 99%.

$^1$H NMR (400 MHz, D2O) δ (ppm): 9.58 (d, 4H); 8.77 (t, 1H); 8.65 (d, 1H); 7.54 (dd, 1H); 7.41 (m, 1H); 7.30 (m, 2H), 7.16 (t, 1H) 5.90 (s, 2H).

Example 2

Synthesis of Compound (10)

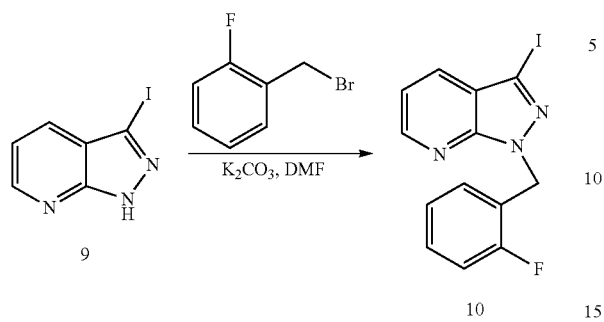

Add 40 g (0.163 mol, 1.0 eq) of 3-iodo-1H-pyrazolo[3,4-b]pyridine, 86.25 g (0.245 mol, 1.5 eq) of o-fluorobenzyl bromide and 45 g (0.327 mol, 1.5 eq) of $K_2CO_3$ dissolved in 500 mL of DMSO into a 1 L 4-neck flask and react for 10 h at room temperature. Pour it into water after thorough reaction as monitored by TLC and drying through concentration, stir to appear a plenty of grey solid, filter and recrystallize PE:EA=5:1 to obtain 404 g of light yellow solid, with a yield of 69.5%.

$^1$H NMR (400 MHz, CDCl3) δ (ppm): 8.62 (d, 1H), 7.85 (d, 1H), 7.27 (dd, 1H), 7.11 (dd, 1H); 6.96-7.08 (m, 3H), 5.82 (s, 2H).

Synthesis of Compound (6)

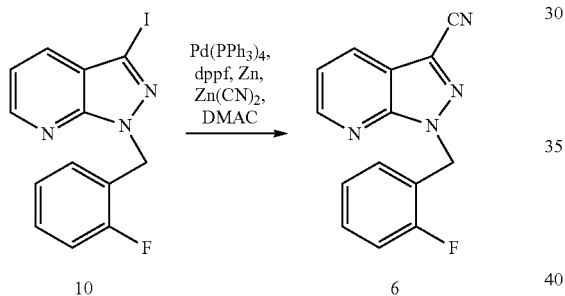

Add 62.5 g (0.177 mol, 1.0 eq) of compound (10), 1.18 g (0.018 mol, 0.1 eq) of zinc powder, 4.91 g (0.00885 mol, 0.05 eq) of dppf, 2.50 g (0.212 mol, 1.2 eq) of $Zn(CN)_2$, 20.8 g (0.018 mol, 0.1 eq) of $Pd(PPh_3)_4$ and 750 mL of DMAC into a 10 L 4-neck flask in turn, heat them till 150° C. and react for 10 h. Add 1 L of DCM after thorough reaction as monitored by TLC and wash with a plenty of water. Extract the aqueous layer with DCM, merge the organic phases, dry with anhydrous sodium sulfate, remove a half of solvent through reduced pressure distillation, pass an appropriate amount of silica gel layer, filter, wash with dichloromethane and concentrate to obtain 27.2 g of light yellow solid. The yield is 63.7%.

$^1$H NMR (400 MHz, CDCl3) δ (ppm): 8.73 (d, 1H); 8.23 (dd, 1H); 7.39 (dd, 1H); 7.26-7.33 (m, 2H); 7.03-7.19 (m, 2H); 5.83 (s, 2H).

The invention claimed is:

1. A method for preparing compound (11), comprising:

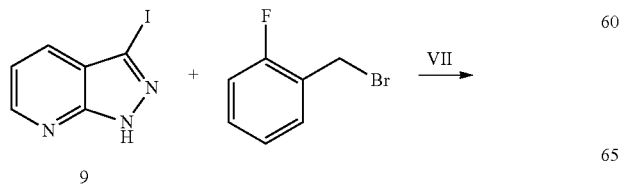

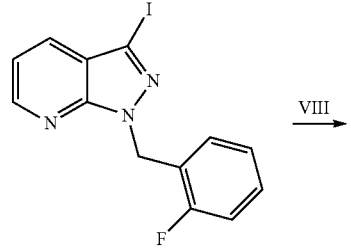

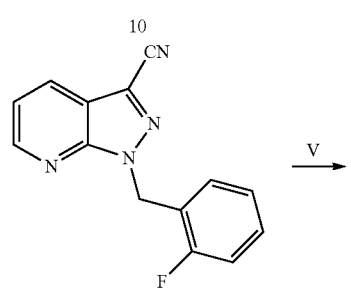

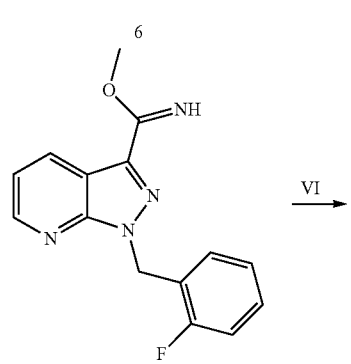

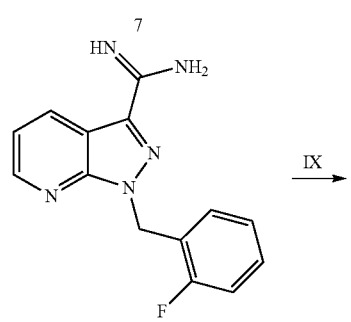

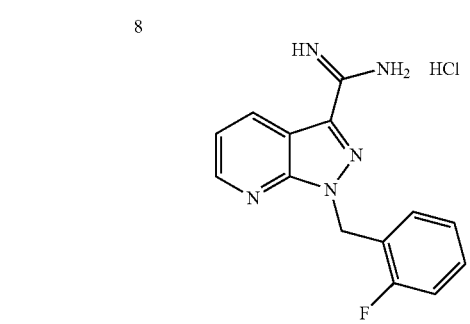

wherein: the reaction condition in step VII: adding potassium carbonate;
the reaction condition in step VIII: adding zinc powder, zinc cyanide, 1,1'-bis(diphenylphosphine) ferrocene and tetra(triphenylphosphine)palladium;

the reaction condition in step V: adding methanol and sodium methoxide;

the reaction condition in step VI: adding ammonium chloride and acetic acid;

the reaction condition in step IX: adding hydrochloric acid or inputting hydrogen chloride.

2. The preparation method according to claim 1, wherein the molar ratio of compound (9): o-fluorobenzyl bromide: potassium carbonate is 1:1~1.5:1.5~3.0.

3. The preparation method according to claim 1, wherein in step VII, the reaction solvent is tetrahydrofuran, N,N-dimethylformamide or dimethylsulfoxide.

4. The preparation method according to claim 1, wherein in step VIII, the reaction temperature is 100~150° C. and the reaction solvent is N,N-dimethylacetamide.

5. The preparation method according to claim 1, wherein in step VIII, the molar ratio of compound (10) and zinc cyanide is 1:0.7~1:1.2.

6. The preparation method according to claim 1, wherein in step IX, the reaction solvent is methyl tertiary butyl ether.

* * * * *

UNITED STATES PATENT AND TRADEMARK OFFICE
CERTIFICATE OF CORRECTION

PATENT NO. : 8,957,210 B2
APPLICATION NO. : 14/364040
DATED : February 17, 2015
INVENTOR(S) : Li et al.

It is certified that error appears in the above-identified patent and that said Letters Patent is hereby corrected as shown below:

References Cited, title page, under Other Publications "(BAY 63/2521)" should be
--(BAY 63-2521)--

In the Claims

Claim 2, Col. 11, line 9 "1:1~" should be --1:1.0~--

Signed and Sealed this
Second Day of June, 2015

Michelle K. Lee
*Director of the United States Patent and Trademark Office*